(12) United States Patent
Hollingsworth et al.

(10) Patent No.: US 6,288,239 B1
(45) Date of Patent: Sep. 11, 2001

(54) 5-TRITYLOXYMETHYL-OXAZOLIDINONES AND PROCESS FOR THE PREPARATION THEREOF

(75) Inventors: Rawle I. Hollingsworth, Haslett, MI (US); Guijun Wang, New Haven, CT (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/665,508

(22) Filed: Sep. 19, 2000

(51) Int. Cl.⁷ .................................................. C07D 263/24
(52) U.S. Cl. ............................................................... 548/232
(58) Field of Search .................................. 548/232

(56) References Cited

U.S. PATENT DOCUMENTS

| | | | |
|---|---|---|---|
| 5,122,601 | * 6/1992 | Sachinvala | ........................... 536/125 |
| 5,292,939 | 3/1994 | Hollingsworth . | |
| 5,319,110 | 6/1994 | Hollingsworth . | |
| 5,374,773 | 12/1994 | Hollingsworth . | |
| 5,808,107 | 9/1998 | Hollingsworth . | |
| 5,837,870 | 11/1998 | Pearlman et al. . | |

FOREIGN PATENT DOCUMENTS

WO 00/06532 * 2/2000 (IT) ............................. C07C/229/00

OTHER PUBLICATIONS

Diekema, D.J., et al., Drugs 59 7–16 (2000).
Hollingsworth, R.I. Biotechnology Annual Review 2 281–291 (1996).
Hollingsworth, R.I., J. Org. Chem. 64 7633–7634.
Wang, G., et al., J. Org. Chem. 64 1036–1038 (1999).
Garcia–Urdiales et al, Feb. 26, 1999, Enzymatic ammonolysis of ethyl (±)–4–chloro–3–hydroxybutanoate. Chemoenzymatic synthesis of both enantiomers of pyrrolidin–3–ol and 5–(chloromethyl)–1,3–oxazolidin–2–one, Tetrahedron: Asymmetry, pp. 721–726.*
Fieser andf Fieser, 1957, Introduction to Organic Chemistry, Library of Congrss Catalog No. 57–6310, D.C. Heath and Co., Boston, MA.*
Fieser and Fieser, 1967, Reagents for Organic Synthesis, Library of Congrss Catalog No. 66–27894, John Wiley and Co., New York, NY.*

* cited by examiner

*Primary Examiner*—Bruck Kifle
*Assistant Examiner*—Rao Uppu
(74) *Attorney, Agent, or Firm*—Ian C. McLeod

(57) ABSTRACT

A method for preparing protected, preferably chiral, 5-trityloxymethyl-oxazolidinone in one step directly from optically active 3-hydroxy-4-trityloxy butyramide is described. Oxazolidinones are an important class of molecules in the pharmaceutical industry especially in the areas of antimicrobials and behavioral disorders.

13 Claims, No Drawings

5-TRITYLOXYMETHYL-OXAZOLIDINONES AND PROCESS FOR THE PREPARATION THEREOF

CROSS-REFERENCE TO RELATED APPLICATION

None

STATEMENT REGARDING FEDERALLY SPONSORED RESEARCH OR DEVELOPMENT

None

BACKGROUND OF THE INVENTION (1) Field of the Invention

The present invention relates to a one-step route to 5-trityloxymethyl-oxazolidinone from 3-hydroxy-4-trityloxy butyramide. In particular, the present invention relates to the preparation of chiral forms of the 5-trityloxymethyl-2-oxazolidinone.

(2) Description of Related Art

Optically pure oxazolidinones can be obtained by carbonylation of vicinal amino alcohols with reagents such as phosgene, ethyl chloroformate and carbonyl imidazole. The preparation of optically-pure 5-trityloxymethyl-oxazolidinone would normally require the preparation of the corresponding optically-pure 5-hydroxymethyl-oxazolidinone followed by a tritylation step to produce 5-trityloxymethyl oxazolidinone.

Oxazolidinones have emerged as a very important class of compounds in drug development especially in the areas of antimicrobials (Diekema, D. J., et al., Drugs 59 7–16 (2000)) and behavioral disorders (Brenner, R., et al., Clin. Therapeut. 22 4 411–419 (2000)). They are especially active against some of the most resistant human pathogens including vancomycin-resistant enterococci, methicillin-resistant *Staphylococcus aureus*, cephalosporin-resistant *Streptococcus pneumoniae* and several organisms that display penicillin resistance (Diekema, D. J., et al., Drugs 59 7–16 (2000)). Linezolid (4) was recently recommended for approval for the treatment of infections from antibiotic resistant bacterial strains especially those that are resistant to vancomycin.

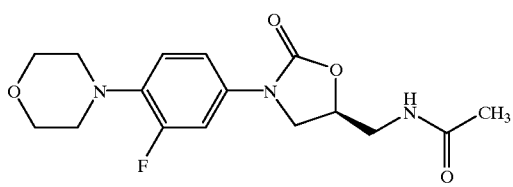

Optically active 3,4-dihydroxybutanoic acids and their γ-lactones are important sources of chirality. They can be obtained in commercial quantities from carbohydrates such as starch, lactose, maltodextrins, cellulose and arabinose by oxidative degradation (Hollingsworth, R. I. Biotechnology Annual Review 2 281–291 (1996); Hollingsworth, R. I., J. Org. Chem. 64 7633–7634 (1999)). See also U.S. Pat. Nos. 5,292,939, 5,808,107, 5,319,110 and 5,374,773 to Hollingsworth. Chiral amino propane diols can be made by Hoffman degradation of the isopropylidene acetals of optically active 3,4-dihydroxybutyric acid amides (Wang, G., et al., J. Org. Chem. 64 1036–1038 (1999)).

SUMMARY OF THE INVENTION

The present invention relates to A process for the preparation of 5-trityloxymethyl-oxazolidinone which comprises:

(a) reacting with stirring a 4-trityl ether of 3,4-dihydroxybutyramide with an alkali or alkaline earth hypohalite in water in the presence of an alkali alkaline earth metal hydroxide and an organic solvent in a reaction mixture to produce the 5-trityloxymethyl-oxazolidine;

(b) separating the 5-trityloxymethyl-oxazolidinone from the reaction mixture in the organic solvent; and (c) removing the organic solvent to produce the 5-trityloxymethyl-oxazolidinone.

The present invention also relates to the novel 5-trityloxymethyl-oxazolidinone 1 produced by the process. Preferably the compounds are chiral.

OBJECTS

It is thus an object of the present invention to provide a one step process enabling the production of novel 5-trityloxymethyl-oxazolidinone from a trityl ether of an amide. Further, it is an object of the present invention to provide for the preparation of chiral products. Further still, it is an object of the present invention to provide a process which is relatively simple and economical by comparison to the prior art and produces the product in high yield and purity. These and other objects will become increasingly apparent by reference to the following description.

DESCRIPTION OF PREFERRED EMBODIMENTS

The reaction involved in the present process is as follows in Scheme 1

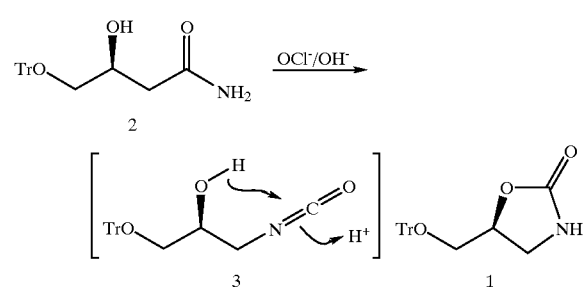

where Tr is a trityl (triphenylmethyl) group. The bracketed compound (3) is a hypothesized isocyanate intermediate which is unstable and forms the ring structure of the 5-trityloxymethyl-2-oxazolidinone (1) from the starting 3-hydroxy-4-trityloxybutyramide 2. The preferred product is the chiral (S)-5-trityloxymethyl-oxazolidinone.

In Scheme 1, the alkali metal hydroxide can be lithium, sodium or potassium hydroxide. The alkaline earth metal hydroxide can be calcium hydroxide, or magnesium hydroxide. Preferably there is an excess of 2 to 6 moles of OH⁻ over the moles of the 4-trityl ether of the amide.

The hypohalite(OCl⁻ or OBr⁻) can also be an alkali metal or alkaline earth metal hypohalite as discussed above for the base. Usually the alkaline earth metal is the same for both OH⁻ and OCl⁻ or OBr⁻; however they can be different.

Most preferably the reaction in step (a) is conducted with an organic solvent which form a 2-phase system with water under the reaction conditions. Besides tetrahydrofuran other solvents are dioxane, propanol and ether. The yields are better with the organic solvent, probably since the product 1 separates into the organic solvent as it is formed. The reaction is conducted at a temperature between about 10° and 80° C. and at atmospheric pressures. The reaction is complete in 6 to 8 hours at 55°–60° C.

The product 1 is purified by removing the miscible organic solvent by evaporation or other means and recrystallizing from a second organic solvent. Dichloromethane is preferred; however other solvents are chloroform, hexanes, alcohol or mixtures of these.

The 4-trityl ether of 3,4-dihydroxybutyramide in step (a) is prepared by reacting excess trityl chloride (preferably in a molar ratio 1.1 to 1.5 to 1 based upon the amide). Other halides such as Br, F or I could be used. The amine base is preferably pyridine although other amines such as triethylamine can be used to react with the HCl or other acid produced in the reaction. The organic solvent is preferably a mixture of dimethyl formamide and tetrahydrofuran with the exclusion of water. The solvent is removed preferably by vacuum and then the ether is washed with hexane to remove excess trityl chloride. The temperature is between about 5° and 40° C. and the pressures are atmospheric. The reaction is complete in 24 to 48 hours. This trityl ether is then used to form the oxazolidinone.

Thus this invention provides a trityl protected, optically pure 5-hydroxymethyl-oxazolidinone such as (S)-5-trityloxymethyl-2-oxazolidinone (1) in a simple high-yield process from optically active 3-hydroxy-γ-butyrolactone using the 4-O-trityl ether of chiral 3,4-dihydroxybutyramide as the starting material.

Because an isocyanate that is hydrolyzed with water is an intermediate species in the Hoffman rearrangement, in principle a vicinal hydroxyl group can act as a nucleophile resulting in cyclization to form an oxazolidinone system. In the present invention, a separate carbonylation reaction using phosgene, ethyl chloroformate or some similar reagent would be avoided. This is illustrated in Scheme 1 for the 4-trityl ether of (S)-3,4-dihydroxybutyric acid amide (2) via the isocyanate 3.

The overall process involves essentially only two steps, only one of which involves the formation of the oxazolidinone 1. The first step is the preparation of the trityl ether from the dihydroxybutyamide 2, a known compound. This amide is obtained in quantitative yield by treating the 3-hydroxy-γ-butyrolactone with aqueous ammonia at room temperature. The second step is the rearrangement of the trityl ether (2) under conditions where the intermediate isocyanate (3) is protected from water, allowing the neighboring hydroxyl group to participate, whilst protecting the final product from base hydrolysis. Hoffman rearrangement using a 2-phase solvent system, in this case tetrahydrofuran/water, gave the protected hydroxymethyl oxazolidine 1 directly in >90% isolated yield and in >99% optical purity. This represents a very significant economy in the synthesis of an important, optically-pure, protected 5-(hydroxymethyl)-2-oxazolidinone in essentially 4 steps from starch, maltose, lactose or similar 4-linked carbohydrate source. The trityl group can be selectively removed allowing the hydroxymethyl function to be transformed into a wide variety of substituents. The ring nitrogen can also be alkylated or actylated by replacing the hydrogen. These two features allow ready access to a large spectrum of possible drug candidates.

EXAMPLE

The following are the steps in preparing the protected 5-trityloxymethyl-oxalidinone.

Preparation of 3-Hydroxy-4-trityloxy Butyramide (2)

11.9 g (0.10 mol) (S)-3,4-dihydroxy-butyramide was dissolved in 50 ml of tetrahydrofuran and 50 ml of dimethylformamide and 10 ml of pyridine followed by 30.6 g (0.11 mol) of trityl chloride was added to the flask. A drying tube filled with calcium chloride was used to exclude moisture. The reaction mixture was stirred at room temperature for 36 hours. After this period of time, it was filtered to remove the solid. The liquid was concentrated under reduced pressure to remove most of the solvent. The solution was poured into ice water, stirred for half an hour and the water layer was removed from the trityl protected amide. The product which was obtained as a semicrystalline liquid was dried under vacuum. The excess trityl chloride was washed away by trituration with hexane. The yield was 33.0 g (91%). Physical data: m.p. 59.0–60.0° C. (from solvent dichloromethane:hexane:acetone=6:3:0.5) $[\alpha]^{25}_D=-53.5°$ (c=0.5,, methanol). $^1$H NMR (300 MHz, CDCl$_3$) δppm, 7.50–7.20 (m, 15 H), 6.17 (s, 1H), 5.62 (s, 1H), 4.19 (m, 1H), 3.17 (d, 2H, J=5.7 Hz), 2.41 (m, 2H). $^{13}$C NMR (75 MHz, CDCl$_3$) δppm, 174.8, 143.5, 128.3, 127.5, 126.7, 86.3, 67.4, 39.2. FTIR cm$^{-1}$ 3345, 1667, 1600, 1490, 1448, 1218, 1074, 763, 703.

Preparation of the (S)-5-trityloxymethyl-2-oxazolidinone (1)

3-Hydroxy-4-trityloxy butyramide 3 3.61 g (0.01 mol) was dissolved in 30 ml THF. Fifteen ml of 13% sodium hypochlorite solution was added to the solution and the mixture was stirred vigorously and then 1.6 g of sodium hydroxide dissolved in 10 ml of water was added. The reaction was stirred at 55–60° C. for 8 hours after which time the rearrangement was completed as indicated by TLC and $^1$H NMR spectroscopy. The THF layer was separated from the water layer. The water layer was extracted 3 times with THF. The combined organic layers was concentrated to remove solvent. The residue was taken up in dichloromethane and the solution dried over sodium sulfate. It was concentrated to remove solvent again and oxazolidinone was obtained as white crystalline product (3.4 g, yield 95%). This crude product normally did not need further purification. M.p. (Solvent: chloroform:hexane:acetone=6:3:1), 206.0–207.0° C. $[\alpha]^{25}_{D=+}35.5°$ (c=1.0, methanol). $^1$H NMR (300 MHz, CDCl$_3$) δppm, 7.50–7.20 (m, 15 H), 5.88 (s, 1H), 4.75 (m, 1H), 3.61 (m, 1H), 3.45 (m, 1H), 3.40 (dd, 1H, J=10.2, 4.5 Hz), 3.23 (dd, 1H, J=10.2, 4.5 Hz) $^{13}$C NMR (75 MHz, CDCl$_3$) δppm 159.8, 143.4, 128.6, 127.9, 127.2, 86.8, 75.4, 64.2, 42.6. IR cm$^{-1}$ 3272, 1753, 1489, 1448, 1085, 748.5 705.5. MS (FAB) low res, MH$^+$ 360.19. HRMS:MH$^+$ C$_{23}$H$_{22}$NO$_3$, 360.1590, theoretical molecular mass 360.1600. The optical purity of the product was >99.9% e.e. based on GC analysis of (S)-(-)-α-Methoxy-α-(trifluoromethyl)phenylacetic acid (Mosher's acid) derivative after deprotection with HBr/acetic acid.

One skilled in the art can deprotect the 5-tritoxymethyl-2-oxazlidinone in the customary fashion (e.g. hydrogenolysis or HBr treatment) and use it for the preparation of important 5-acetamidomethyl oxazolidinones (as described in various patents, e.g. Pearlman et al U.S. Pat. No. 5,837, 870. The hydroxyl group can be converted to a nitrogen-containing function by any of the methods that are known. These include mesylation or tosylation followed by displacement with ammonia, azide, benzylamine and other nitrogen nucleophiles as shown in Scheme 2.

Scheme 2

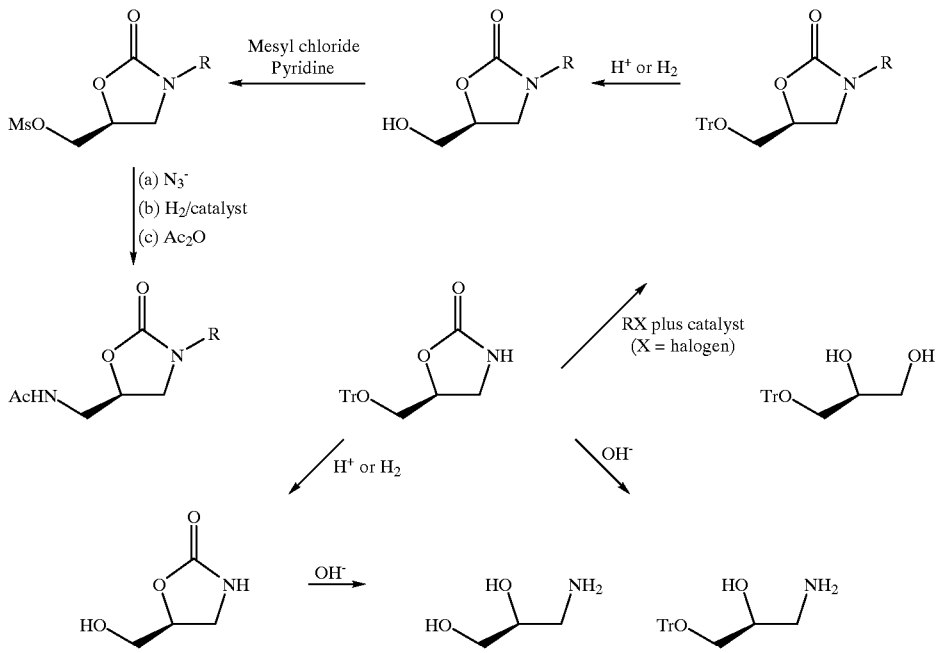

It is intended that the foregoing description be only illustrative of the present invention and that the present invention be limited only by the hereinafter appended claims.

We claim:

1. A process for the preparation of 5-trityloxymethyl-2-oxazolidinone which comprises:
   (a) reacting with stirring a 4-trityl ether of 3,4-dihydroxybutyramide with an alkali or alkaline earth hypohalite in water in the presence of an alkali or alkaline earth metal hydroxide and an organic solvent in a reaction mixture to produce the 5-trityloxymethyloxazolidine;
   (b) separating the 5-trityloxymethyl-2-oxazolidinone from the reaction mixture which is separated from the water in the organic solvent; and
   (c) removing the organic solvent to produce the 5-trityloxymethyl-2-oxazolidinone.

2. The process of claim 1 wherein the alkali or alkaline earth metal hydroxide is sodium hydroxide.

3. The process of claims 1 or 2 wherein the organic solvent is separated from the water in step (b) by layer separation.

4. The process of claim 1 wherein the organic solvent is removed by evaporation.

5. The process of claim 1 wherein after step (c) the 5-tritylmethyl-2-oxazolidinone is purified by being dissolved in dichloromethane over a drying agent and then the dichloromethane is removed.

6. The process of claim 1 wherein the 4-trityl ether of 3,4-dihydroxybutyramide in step (a) is prepared by reacting excess trityl chloride with 3,4-dihydroxbutyramide in an organic solvent in the presence of an amine base, to produce the 4-trityl ether which is washed with water which is removed and then the excess trityl chloride is removed by solvent extraction.

7. The process of claim 1 wherein the organic solvent is tetrahydrofuran.

8. The process of claim 1 wherein the organic solvent is dioxane.

9. The process of claim 1 wherein hypohalite is hypochlorite.

10. The process of claim 1 wherein the hypohalite is hypobromite.

11. The process of claim 1 wherein the organic solvent is water-insoluble alcohol.

12. The process of any one of claims 1, 2, 4, 5, 6, 7, 8, 9, 10 or 11 wherein the 5-trityloxymethyl-2-oxazolidinone is optically pure.

13. 5-Trityloxymethyl-2-oxazolidinone.

* * * * *